US010226227B2

United States Patent
Sadeghi-Naini et al.

(10) Patent No.: US 10,226,227 B2
(45) Date of Patent: Mar. 12, 2019

(54) SYSTEM AND METHOD FOR CLASSIFYING AND CHARACTERIZING TISSUES USING FIRST-ORDER AND SECOND-ORDER STATISTICS OF QUANTITATIVE ULTRASOUND PARAMETRIC MAPS

(71) Applicant: SUNNYBROOK RESEARCH INSTITUTE, Toronto (CA)

(72) Inventors: Ali Sadeghi-Naini, North York (CA); Hadi Tadayyon, North York (CA); Gregory J. Czarnota, Oakville (CA); Omar Falou, Toronto (CA)

(73) Assignee: SUNNYBROOK RESEARCH INSTITUTE, Ontario (CA)

( * ) Notice: Subject to any disclaimer, the term of this patent is extended or adjusted under 35 U.S.C. 154(b) by 374 days.

(21) Appl. No.: 14/893,319

(22) PCT Filed: May 23, 2014

(86) PCT No.: PCT/CA2014/050480
§ 371 (c)(1),
(2) Date: Nov. 23, 2015

(87) PCT Pub. No.: WO2014/186899
PCT Pub. Date: Nov. 27, 2014

(65) Prior Publication Data
US 2016/0120502 A1    May 5, 2016

Related U.S. Application Data

(60) Provisional application No. 61/827,369, filed on May 24, 2013.

(51) Int. Cl.
A61B 8/14    (2006.01)
A61B 8/08    (2006.01)
(Continued)

(52) U.S. Cl.
CPC .................. *A61B 8/14* (2013.01); *A61B 8/08* (2013.01); *A61B 8/085* (2013.01); *A61B 8/5207* (2013.01);
(Continued)

(58) Field of Classification Search
CPC ......... A61B 8/08; A61B 8/0825; A61B 8/085; A61B 8/14; A61B 8/469; A61B 8/5207;
(Continued)

(56) References Cited

U.S. PATENT DOCUMENTS

| | | |
|---|---|---|
| 2005/0165290 A1 | 7/2005 | Kotsianti et al. |
| 2010/0063393 A1 | 3/2010 | Moradi et al. |
| 2010/0098306 A1 | 4/2010 | Madabhushi et al. |

FOREIGN PATENT DOCUMENTS

| | | |
|---|---|---|
| WO | 2012065151 A1 | 5/2012 |
| WO | 2013049153 A2 | 4/2013 |

OTHER PUBLICATIONS

International Search Report and Written Opinion under dated Oct. 7, 2014 in connection with PCT/CA2014/050480.
(Continued)

*Primary Examiner* — Mark Remaly
(74) *Attorney, Agent, or Firm* — Quarles & Brady LLP (57) ABSTRACT

Systems and methods for classifying tissue using quantitative ultrasound techniques. Parameters are calculated directly from raw echo signal data acquired from a region-of-interest during an ultrasound scan and parametric maps are produced using these parameters. These parameters can be calculated after normalizing the echo signal data using reference data so as to mitigate the effects of variations in instruments settings, ultrasound beam diffraction, and attenuation effects. First-order and second-order statistical measures are computed from these parametric maps, and are used to classify the tissue or tissues in the region-of-interest.
(Continued)

Using these systems and methods, tissue can be classified with different levels of classification. For example, a tissue characterized as malignant cancer can additionally be graded (e.g., Grade I, II, or III).

19 Claims, 7 Drawing Sheets

(51) Int. Cl.
| | | |
|---|---|---|
| *G06T 7/00* | (2017.01) | |
| *G01N 33/483* | (2006.01) | |
| *G06T 7/11* | (2017.01) | |
| *G06K 9/62* | (2006.01) | |
| *A61B 8/00* | (2006.01) | |

(52) U.S. Cl.
CPC ....... *A61B 8/5223* (2013.01); *G01N 33/4833* (2013.01); *G06K 9/6212* (2013.01); *G06K 9/6269* (2013.01); *G06T 7/0012* (2013.01); *G06T 7/11* (2017.01); *A61B 8/0825* (2013.01); *A61B 8/469* (2013.01); *A61B 8/587* (2013.01); *G06K 2209/053* (2013.01); *G06T 2207/10132* (2013.01); *G06T 2207/30024* (2013.01); *G06T 2207/30096* (2013.01); *G06T 2207/30204* (2013.01)

(58) Field of Classification Search
CPC .. A61B 8/5223; A61B 8/587; G01N 33/4833; G06K 2209/053; G06K 9/6212; G06K 9/6269; G06T 2207/10132; G06T 2207/30024; G06T 2207/30096; G06T 2207/30204; G06T 7/0012; G06T 7/11
See application file for complete search history.

(56) References Cited

OTHER PUBLICATIONS

Lizzi et al., Statistics of Ultrasonic Spectral Parameters for Prostate and Liver Examinations, IEEE Transactions on Ultrasonics, Ferroelectrics, and Frequency Control, vol. 44, No. 4, Jul. 1998, pp. 935-942.

Lin et al., Ultrasound Backscatter Spectral Analysis Proivdes Image Feedback for Histotripsy Tissue Fractionation, 2011 IEEE International Ultrasonics Symposium Proceedings, pp. 33-36.

Kolios et al., Towards Understanding the Nature of High Frequency Backscatter from Cells and Tissues: an investigation of Backscatter Power Spectra from Different Concentrations of Cells of Different Sizes, 2004 IEEE Ultrasonics Symposium, vol. 1, pp. 606-609.

SYSTEM AND METHOD FOR CLASSIFYING AND CHARACTERIZING TISSUES USING FIRST-ORDER AND SECOND-ORDER STATISTICS OF QUANTITATIVE ULTRASOUND PARAMETRIC MAPS

CROSS-REFERENCE TO RELATED APPLICATIONS

This application represents the national stage entry of PCT International Application No. PCT/CA2014/050480 filed May 23, 2014, which claims the benefit of U.S. Provisional Patent Application Ser. No. 61/827,369, filed May 24, 2013, the contents of which are hereby incorporated herein by reference in their entirety for all purposes.

BACKGROUND OF THE INVENTION

The field of the invention is systems and methods for quantitative ultrasound ("QUS"). More particularly, the invention relates to systems and methods for classifying and characterizing tissues as being associated with a particular histological state using QUS.

Clinical ultrasound is a useful, and noninvasive tool for diagnosing cancer and other diseases. In addition to ultrasound's ability to non-invasively differentiate malignant tumors from their benign counterpart, the ability to characterize a malignant tumor in terms of its histological grade is of paramount importance for staging and treatment design. Due to the many instrument parameters that can be chosen during an ultrasound imaging session, however, a comparative interpretation of conventional B-mode images becomes difficult when different ultrasound machines are used, or when different settings are applied. Additionally, B-mode images lack information about microstructural properties of soft tissues.

Quantitative ultrasound ("QUS") techniques, which examine the frequency-dependent backscatter of tissues independent of the instrument settings, have been suggested to overcome this limitation. Such techniques have been applied in-vivo to reveal information about the tissue's underlying microstructure, or histological state, enabling the differentiation of disease from non-disease, the differentiation of viable from apoptotic tissue, and the characterization of a disease into its subtypes. Specifically, parameters including effective scatterer diameter ("ESD") and effective acoustic concentration ("EAC") have demonstrated the potential to distinguish between mouse tumor models of mammary carcinoma and fibroadenoma. However, the estimation of effective scatterer size and acoustic concentration require prior knowledge about the backscattering model, which can often be complicated to characterize in the case of tissue particular tissues.

To avoid complex model fitting, basic spectral parameters extracted via a linear regression analysis of the radio frequency ("RF") echo signal spectrum, including mid-band fit ("MBF"), spectral slope ("SS"), and spectral 0-MHz intercept ("SI"), were proposed for tissue characterization. Such quantitative parameters have been previously used to characterize various types of tissue abnormalities, including those in prostate, lymph nodes, and myocardium, and to detect apoptotic cell death. By modeling the ultrasonic power spectrum as an acoustic impedance autocorrelation function, it has been demonstrated that SS can be related to effective scatterer size, SI can be related to acoustic concentration, and MBF can be related to both effective scatterer size and acoustic concentration. Alternatively, scatterer spacing, also known as spacing among scatterers ("SAS"), has been investigated as a tissue characterizing parameter when the tissue of interest contained detectable periodicity in its structural organization. In this context, scatterer spacing has been applied to characterize human breast tumors by categorizing them into normal, fibroadenoma, simple carcinoma, or infiltrating papillary carcinoma. Other studies have also investigated the potential of SAS for characterizing diffuse diseases of the liver.

While the conventional quantitative ultrasound mean parameters discussed above describe the frequency-dependent properties of tissue microstructure, textural characteristics of their parametric maps can provide second-order statistics by quantifying the patterns of gray-level transitions. A number of previous studies have applied the textural features of ultrasound B-mode images to distinguish between malignant and benign breast tumors. The principle behind this tissue classification technique is that malignant tumors tend to present as heterogeneous internal echoes, while benign tumors often demonstrate homogeneous internal echoes. Textural analysis techniques aim at extracting the tissue internal echo properties or "texture," based on the ultrasonic gray-level transitions, and hence can define differentiable characteristics in this application. However, conventional B-mode images may also present undesirable variations in textural estimates due to variations in instrument settings, ultrasound beam diffraction, and attenuation effects.

It would therefore be desirable to provide systems and methods for classifying tissues as being associated with particular histological states using ultrasound, but without the limitations in accuracy that are associated with analyzing B-mode images. Advantageously, such systems and methods would be capable of classifying tissues based on histological states including both general classifications (e.g., normal, cancerous) and subtype classifications (e.g., tumor grade, liver fibrosis stage).

SUMMARY OF THE INVENTION

The present invention overcomes the aforementioned drawbacks by providing systems and method for classifying tissues by analyzing first-order and second-order statistics of quantitative ultrasound parametric maps, in which undesirable variations in textural estimates due to variations in instruments settings, ultrasound beam diffraction, and attenuation effects, are substantially mitigated.

It is an aspect of the invention to provide a method for classifying a tissue as being associated with a particular histological state using an ultrasound system. Ultrasound echo signal data is acquired from a region-of-interest that contains the tissue, using the ultrasound system. At least one parametric map is produced from the acquired ultrasound echo signal data. The at least one parametric map has pixel values associated with a parameter computed from the acquired ultrasound echo signal data. At least one first-order statistical measure of the at least one parametric map is computed, such as a mean. At least one second-order statistical measure of the at least one parametric map is also computed, such as a contrast, energy, homogeneity, or correlation. The tissue is then classified as being associated with a particular histological state using the computed at least one first-order statistical measure and the computed at least one second-order statistical measure.

It is another aspect of the invention to provide a method for generating an imaging biomarker that is indicative of a histological state of a tissue using an ultrasound system.

Ultrasound echo signal data is acquired from a tissue using the ultrasound system. At least one parametric map is then produced from the acquired ultrasound echo signal data. The at least one parametric map has pixel values associated with a parameter computed from the acquired ultrasound echo signal data. At least one first-order statistical measure of the at least one parametric map is computed, as is a plurality of second-order statistical measures of the at least one parametric map. An imaging biomarker is then generated by determining a combination of the computed at least one first-order statistical measure and the computed plurality of second-order statistical measures that is correlated with a desired accuracy of classifying the tissue as being associated with a particular histological state. The desired accuracy may be a desired specificity, sensitivity, or combination of both.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Described here are systems and methods for characterizing tissue using quantitative ultrasound techniques. Parameters are calculated directly from raw echo signal data acquired from a region-of-interest during an ultrasound scan. Preferably, these parameters are calculated after normalizing the echo signal data using reference data so as to mitigate the effects of variations in instruments settings, ultrasound beam diffraction, and attenuation effects. For instance, quantitative ultrasound ("QUS") parameters such as mid-band fit ("MBF"), spectral slope ("SS"), spectral 0-Mhz intercept ("SI"), spacing among scatterers ("SAS"), effective scatterer diameter ("ESD"), and effective acoustic concentration ("EAC") can be computed, from which parametric maps associated with the region-of-interest are generated. First-order and second-order statistical measures are computed from these parametric maps, and are used to characterize the tissue or tissues in the region-of-interest. Using these systems and methods, tissue can be characterized in different levels of classification. For instance, a tissue characterized as malignant cancer can additionally be graded (e.g., Grade I, II, or III), and tissue characterized as fibrotic liver can additionally be characterized based on stage of liver fibrosis. As such, the systems and methods described here provide for non-invasive, highly accurate characterization and grading of tissues.

Figure 1:
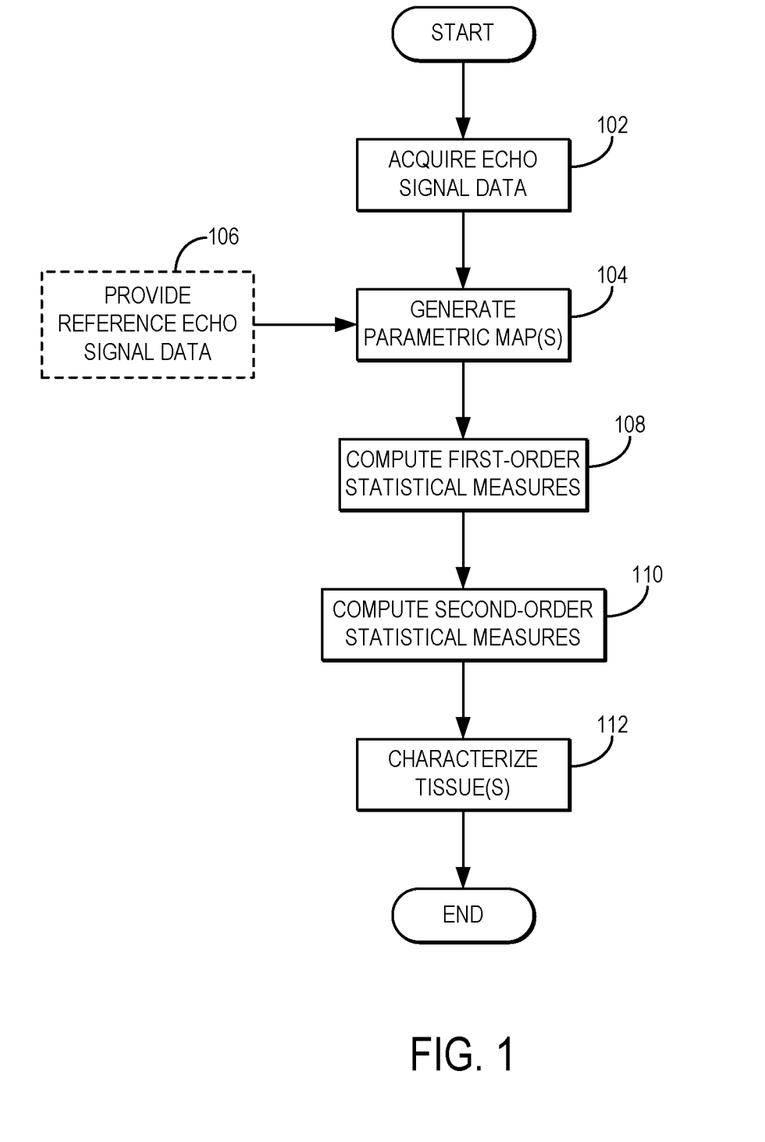
FIG. 1 is a flowchart setting forth the steps of an example of a method for characterizing a tissue using quantitative ultrasound and first-order and second-order statistical measures of quantitative ultrasound parametric maps.

Referring now to FIG. 1, a flowchart setting forth the steps of an example of a method for characterizing a tissue using quantitative ultrasound is illustrated. The method generally begins with the acquisition of ultrasound echo signal data from a region that contains the tissue to be characterized, as indicated at step 102. The echo signal data, also referred to as radio frequency ("RF") data, is acquired in response to ultrasound transmitted to the region-of-interest. The transmitted ultrasound is preferably conventional-frequency, but can also be high-frequency ultrasound. In some instances, it may also be beneficial to use combinations of low-frequency and high-frequency ultrasound depending on the depth of the tissue and the desired imaging resolution. For instance, higher ultrasound frequencies are capable of increasing imaging resolution, but at the cost of limiting the penetration depth of the ultrasound. For example, ultrasound frequencies in the range of 20-60 MHz can achieve imaging resolutions in the range of 30-80 μm, whereas ultrasound frequencies in the range of 1-20 MHz can achieve imaging resolutions of 30 μm to about 1.5 mm.

By way of example, echo signal data can be acquired from a subject using an ultrasound system operating at a conventional ultrasound frequency, such as 6 MHz or 10 MHz. Alternatively, the ultrasound system can be operated to generate high frequency ultrasound, such as greater than 20 MHz. The echo signals can be obtained in a number of differently oriented image planes. Optionally, B-mode images can also be acquired and used to identify one or more region-of-interest ("ROI") containing the tissue or tissues to be characterized. As an example, each selected ROI can then be segmented using a sliding window approach with or without overlap between adjacent windows. Each window is advantageously sized to be larger than the minimum size required to obtain reliable spectral parameters that are independent of window length. For instance, the window can be sized to be larger than ten wavelengths of the transmitted ultrasound.

From the echo signal data, one or more parametric maps are generated, as indicated at step 104. For instance, the parametric maps are images whose pixel values are representative of quantitative ultrasound parameters computed from the raw echo signal data. Examples of such parameters include mid-band fit ("MBF"), spectral slop ("SS"), spectral 0-MHz intercept ("SI"), spacing among scatterers ("SAS"), effective scatterer diameter ("ESD"), and effective acoustic concentration ("EAC"). An example of how these parameters may be calculated is provided below.

First, a mean power spectrum can be computed in each window of a selected ROI by taking the squared magnitude of the Fourier transform of the Hanning gated RF echo, $e_s(t,x_i)$, and averaging the result across the RF lines, $x_i$, $i=N, N+1, \ldots, M$.

In order to make the analysis system-independent, the echo signal data can be normalized on a sliding window basis using reference data obtained from a tissue-mimicking phantom, a planar reflector, or the like. To this end, reference echo signal data can optionally be provided, as indicated at step 106.

For example, a tissue-mimicking phantom composed of agar gel embedded with glass microspheres can be used to obtain reference echo signal data. Preferably, such reference echo signal data can be used for normalizing the mean power spectrum on which linear regression analyses will be performed in order to extract a number of quantitative ultrasound parameters, such as MBG, SS, and SI.

As another example, a planar reflector, such as a Plexiglas planar reflector, can be used to obtain reference echo signal data to be used when computed SAS in order to avoid affecting the estimation of SAS in the tissue by the glass scatterers in the tissue-mimicking phantom. Reference echo signal data obtained from such a planar reflector are preferably obtained at a plurality of different depths to cover the potential tissue depths in the region of the subject. As an example, twelve equally spaced depths ranging from 1-6 cm can be utilized.

For a given data window, the corresponding reference window can be selected by nearest neighbor interpolation. Spectral normalization of the mean power spectrum may be performed using RF echoes obtained from a reference phantom, $e_p(t, x_i)$, to remove the system transfer function. The mean normalized power spectrum, $S(f)$, of a window can be written as, $$S(f) = \frac{\sum_{i=N}^{M} |FFT(e_s(t, x_i))|^2}{\sum_{i=N}^{M} |FFT(e_p(t, x_i))|^2}; \tag{1}$$

where f is frequency and FFT( . . . ) is the Fast Fourier Transform operator. A linear regression analysis, such as a least squares fit, can then be applied to the mean normalized power spectrum to extract the MBF, SS, and SI parameters as follows:

$$S(f)=SS \cdot f + SI \tag{2}$$

$$MBF=SS \cdot f_c + SI \tag{3}$$

where $f_c$ is the frequency at the center of the analysis bandwidth, which may be the −6 dB frequency bandwidth. More generally, the bandwidth can be determined empirically, such as from the power spectrum of a reference phantom.

SAS can be estimated using an autoregressive ("AR") model of the echo signal, as one example. The AR model predicts the output of a stationary stochastic process as a linear combination of previous samples of its output, which can be written as, $$\hat{e}_s[t] = \sum_{k=1}^{p} a_k \hat{e}_s[t-k] + w[t]; \tag{4}$$

where $a_k$ are the AR coefficients, w[t] is a white noise input sequence, and p is the order of the AR model. The power spectrum, $|X(f)|^2$, can be obtained by Fourier transforming both sides of Eqn. (4) as follows, $$|X(f)|^2 = \frac{\delta^2}{\left|1 + \sum_{k=1}^{p} a_k e^{-j2\pi fk}\right|^2}. \tag{5}$$

The normalized AR power spectrum, $S_{AR}(f)$, is obtained similar to Eqn. (1), except that the numerator is an AR-estimated power spectrum, $|X(f)|^2$, and the denominator is reference echo data, $e_r(t_n)$, such as that obtained from a planar reflector as described above. The subscript "n" in $e_r(t_n)$ represents discrete depth intervals at which the reference echo data is obtained. Also, in some instances the reference echo data, $e_r(t_n)$, can be independent of lateral location, $x_i$, as the power spectrum of the reference can be averaged laterally across the entire transducer width, L, to obtain a smooth mean power spectrum. More generally, $$S_{AR}(f, x_i) = \frac{\sum_{i=N}^{M} |X(f, x_i)|^2}{\sum_{i=N}^{M} |FFT(e_r(t_n, x_i))|^2}. \tag{6}$$

The autocorrelation of the normalized AR power spectrum can then be computed as, $$R_{ff}(\Delta f) = \sum_{\Delta f=1}^{N} S(f)S(f - \Delta f); \tag{7}$$

which is termed the spectral autocorrelation ("SAC"). The SAS corresponds to the frequency lag, $\Delta f$, at which the first peak in the SAC occurs, $\Delta f_p$, and thus can be computed as, $$SAS = \frac{c}{2\Delta f_p}; \quad (8)$$

where c is the mean speed of sound in the tissue of interest. As one example, for normal breast tissue, which encompasses both fatty and parenchymal tissue, a sound speed of 1455 m/s can be assumed, while for breast tumors, a sound speed of 1540 m/s can be assumed. These values are consistent with tomography measurements of the speed of sound in the breast.

Other quantitative ultrasound parameters that can be computed from the echo signal data are the effective scatterer diameter ("ESD") and effective acoustic concentration ("EAC"), which can be estimated by fitting a theoretical tissue backscatter model to the measured backscatter signal from the tissue of interest. For example, estimated and theoretical backscatter coefficients ("BSCs") can be used to compute ESD and EAC.

The BSC, $\sigma_b(f)$ is defined as the differential backscattering cross-section per unit volume and is related to the normalized sample power spectrum, $S(f)$, through a scaling factor that includes the gate length, $\Delta z$, aperture area, $A_0$, and the distance between the transducer and the proximal surface of the gated ROI, R. The BSC can thus be computed as follows:

$$\sigma_b(f) = \frac{1.45 \cdot R^2}{(A_0 \cdot \Delta z) S(f)}; \quad (9)$$

The formula for the BSC in Eqn. (9) was originally developed for single-element transducers. For clinical ultrasound applications, where linear array transducers are used, a reference phantom technique can be used to estimate the BSC, $$\hat{\sigma}_{bs}(f) = \frac{S_s(f)}{S_r(f)} \sigma_{br}(f) e^{4(\alpha_s - \alpha_r)(R + \frac{\Delta z}{2})}; \quad (10)$$

where the subscript s denotes sample and the subscript r denotes reference, and $\alpha$ is the attenuation coefficient.

Once the BSC estimate of an ROI in the sample is obtained, the average ESD and EAC for the ROI can be estimated by least squares fitting of the estimated and theoretical BSCs. For the theoretical BSC, the Gaussian form factor can be used. The Gaussian form factor describes spherical scatterers whose acoustic impedance varies continuously with the surrounding material. In contrast to the SAS estimation, which is based on detection of coherent scatterers, the Gaussian form factor is a model for estimating the properties of incoherent scatterers. This form factor has been proven useful for characterizing mouse models of breast cancer and human lymph nodes.

At least one first-order statistical measure of the one or more parametric maps produced in step 104 is computed, as indicated at step 108. In general first-order statistics are computed from a function that measures the probability of a certain pixel occurring in an image and, therefore, depend on individual pixel values and not on the interaction of neighboring pixel values. By way of example, the first-order statistical measure may be the mean of a parametric map. Alternatively, the first-order statistical measure may be the standard deviation, skewness, or kurtosis of a parametric map.

At least one second-order statistical measure of the one or more parametric maps produced in step 104 is also computed, as indicated at step 110. In general, second-order statistics are computed from a probability function that measures the probability of a pair of pixel values occurring at some offset in an image. This probability function is typically referred to as a "co-occurrence matrix" because it measures the probability of two pixel values co-occurring at the given offset. An example of the co-occurrence matrix is the gray level co-occurrence matrix ("GLCM"). These second-order statistics can generally be referred to as textural features of an image. The application of textural analysis on the quantitative ultrasound parametric maps, where instrument dependencies are preferably removed via the aforementioned normalization, provides advantageous information for the tissue characterization techniques described later.

The GLCM represents, statistically, the angular relationship between neighboring pixels as well as the distance between them. Based on the statistical information provided by a GLCM, several textural features can be defined and extracted. By way of example, the second-order statistical measure computed in step 110 may include contrast, energy, homogeneity, or correlation. Alternatively, the second-order statistical measure could include other second-order statistics, including autocorrelation, dissimilarity, GLCM variance, entropy, cluster shade, cluster prominence, and maximum probability Contrast ("CON") represents a measure of difference between the lowest and highest intensities in a set of pixels. Energy ("ENE") measures the frequency of occurrence of pixel pairs and quantifies its power as the square of the frequency of gray-level transitions. Homogeneity ("HOM") measures the incidence of pixel pairs of different intensities; thus, as the frequency of pixel pairs with close intensities increases, HOM increases. Correlation ("COR") measures the intensity correlation between pixel pairs.

The computed parametric maps are processed using a GLCM-based texture analysis process to extract the aforementioned second-order statistical measures, which may also be referred to as textural features, as follows. A GLCM is an $N_g \times N_g$ matrix, where $N_g$ is the number of quantized gray levels in the image for which the GLCM is computed (e.g., the parametric maps in this instance). Each element in the GLCM, $p(i, j)$, is a statistical probability value for changes between the $i^{th}$ and $j^{th}$ gray levels at a particular displacement distance, d, and angle, $\theta$. Thus, given $p(i, j)$ as an element in an $N_g \times N_g$ GLCM, the above-mentioned textural parameters can be defined as follows:

$$CON = \sum_{k=0}^{N_g-1} k^2 \left( \sum_{i=1}^{N_g} \sum_{j=1}^{N_g} p(i, j) \right) \text{ with } k = |i - j|; \quad (11)$$

$$ENE = \sum_{i=1}^{N_g} \sum_{j=1}^{N_g} p(i, j)^2; \quad (12)$$

$$HOM = \sum_{i=1}^{N_g} \sum_{j=1}^{N_g} \frac{p(i, j)}{1 + |i - j|}; \quad (13)$$

-continued $$COR = \frac{\sum_{i=1}^{N_g}\sum_{j=1}^{N_g}(i-\mu_x)(j-\mu_y)p(i,j)}{\sigma_x\sigma_y};$$ (14)

where $\mu_x$ and $\mu_y$ are the means for the columns and rows, respectively, of the GLCM, $$\mu_x = \sum_{i=1}^{N_g}\sum_{j=1}^{N_g} i \cdot p(i,j);$$ (15)

$$\mu_y = \sum_{i=1}^{N_g}\sum_{j=1}^{N_g} j \cdot p(i,j);$$ (16)

and where $\sigma_x$ and $\sigma_y$ are the standard deviations for the columns and rows, respectively, of the GLCM, $$\sigma_x^2 = \sum_{i=1}^{N_g}\sum_{j=1}^{N_g}(i-\mu_x)^2 \cdot p(i,j);$$ (17)

$$\sigma_y^2 = \sum_{i=1}^{N_g}\sum_{j=1}^{N_g}(j-\mu_y)^2 \cdot p(i,j).$$ (18)

A number of different GLCMs can be constructed for each parametric map. For example, sixteen symmetric GLCMs can be constructed considering each pixel's neighbors located at the displacement distances, d, of one to four pixels with angular values, θ, of 0-135 degrees with 45 degree increments. The second-order statistical measures, or textural features, can then be extracted from the corresponding GLCMs of each QUS parametric map and consequently averaged to produce the computed second-order statistical measures. This example results in sixteen second-order statistical measures (CON, ENE, HOM, and COR for each of MBF, SS, SI, and SAS parametric maps), which, as described below, can be applied for distinguishing tumors or other pathologic disease states from normal tissue, as well as for grading tumors and staging other diseases, such as liver fibrosis.

Using the at least one first-order statistical measure and the at least one second-order statistical measure computed earlier, the tissue in the region-of-interest is characterized, as indicated in step 112. For example, the tissue is characterized by identifying a combination of the first-order and second-order statistical measures that is representative of a defined class, such as a tissue state, disease progression state, or tumor grade. As such, combinations of the first-order and second-order statistical measures of the quantitative ultrasound parametric maps can be viewed as defining imaging biomarkers that indicate the histological state of tissue.

The histological state of tissue can include whether the microscopic anatomy of a tissue is normal and healthy, or whether the microscopic anatomy of the tissue is in some way abnormal. The microscopic anatomy of a tissue can be considered abnormal as a result of any number of different processes. For example, a tissue can be characterized as having an abnormal histological state when the tissue is has become cancerous, whether benign or malignant, or affected by other pathologies. As one example, when the tissue is liver, histological states may include liver fibrosis, non-alcoholic fatty liver disease ("NAFLD"), cirrhosis, and ischemic damage of the liver tissue. A tissue can also be characterized as having an abnormal histological state when it has undergone structural changes, such as scarring in response to mechanical, thermal, or other stresses, or when it has undergone apoptosis.

By way of example, a discriminant analysis, such as a linear discriminant analysis ("LDA"), can be implemented to characterize the tissue based on the first-order and second-order statistical measures of the parametric maps. The characterization process can include multiple steps. For instance, the first iteration of characterization can indicate whether a tissue is normal or cancerous. If the tissue is characterized as cancerous, a second iteration of characterization can be performed to grade the tumor by categorizing the tumor into histopathological grades (e.g., Grade I, II, or III).

To characterize tissue using LDA, the linear discriminant can be trained for the tissue being analyzed. Examples of tissues that can be analyzed include, but are not limited to, tissues in the breast, liver, brain, prostate, kidney, bladder, gallbladder, spleen, cervix, blood vessels, muscle, and bone. This training can be performed in real-time or, preferably, can be performed off-line with the results stored in a feature set database that can be provided during processing. Such a feature set database includes combinations of the first-order statistical measures and second-order statistical measures that maximize, or otherwise provide desired levels of, the specificity and sensitivity of the tissue characterization for a given organ (e.g., breast, liver, brain, prostate, kidney, bladder, gallbladder, spleen, cervix, blood vessels, muscle, bone) or tissue type (e.g., brain gray matter, brain white matter). As discussed above, these feature sets can define imaging biomarkers for the specific organ or tissue type and can additionally define imaging biomarkers for tumor grading.

It is also noted that that statistical measures other than first-order or second-order statistics can be computed and implemented in the tissue characterization process. For instance, higher-order statistics of the parametric maps can be computed and included in a feature set. Examples of higher-order statistics include third-order statistics, which consider the relationships among three or more pixels, fourth-order statistics, which consider the relationships among four or more pixels, and so on. Higher-order statistics can also be derived by computing second-order or higher-order statistics of the statistical parameters maps generated by computing the second-order statistics of quantitative ultrasound parametric maps. For instance, higher-order statistics can be computed by first producing a statistical map that indicates a particular second-order statistic of a parametric map and then computing a second-order statistic of that statistical map. This process can be iteratively applied to acquire higher-order statistics if desired.

It will be appreciated by those skilled in the art that each organ and tissue type may have a different feature set that provides the desired accuracy for characterizing a tissue or grading a tumor. In general, a feature set includes at least one first-order statistical measure of at least one parametric map and at least one second-order statistical measure of at least one parametric map. It is contemplated that in at least some instances, a single first-order statistical measure and a plurality of second-order statistical measures computed for each of two or more parametric maps will generally provide clinically acceptable accuracy. Practically, the two or more parametric maps can often include at least MBF, SS, and SI because these three parameters are generally computed together.

It is noted that the computational time of the tissue classification method described above is primarily allocated to generating the parametric maps. As one example, computing MBF, SS, SI, and SAS maps for one subject can take upwards of ten minutes; although, this time can be considerably lessened by using a processor such as a graphics processing unit ("GPU"). Other steps of the method, such as computing the GLCM matrices and textural parameters can be performed on the order of a second or two, and characterization step (e.g., using discriminant analysis) can be performed in a manner of a few milliseconds. Overall, the method can be performed in a clinically-relevant period of time.

As an alternative to using LDA to characterize tissues, other statistical analyses can be implemented. Examples of other statistical analyses that can be implemented include an unpaired t-test for normally distributed data, a Mann-Whitney unpaired test, a pairwise comparison using a paired t-test for normally distributed data, a Wilcoxon paired test for non-parametric data, and a one-way ANOVA test when trying to differentiate more than two tissue types. As an alternative to use LDA, other pattern recognition or machine learning techniques can be used for tissue classification and characterization. Examples of alternative techniques include using artificial neural networks ("ANNs") or a support vector machine ("SVM").

Having described the general steps of a method for characterizing a tissue's histological state using first-order and second-order statistical measures of quantitative ultrasound parameter maps, some examples of implementing this method, and of different clinical applications for such a method, are now described.

In one example, breast tissue can be characterized. The first-order and second-order statistical measures listed in Table 1 below define an example of an imaging biomarker that can achieve 100 percent sensitivity, 97 percent specificity, and 98 percent overall accuracy in characterizing breast tissue as either normal or cancerous. In addition, the same set of measures can further define an imaging biomarker that can achieve 91 percent accuracy in grading the characterized cancerous breast tissue as Grade I, II, or III.

TABLE 1

| First-Order Statistical Measures | Second-Order Statistical Measures |
| --- | --- |
| Mean of MBF | CON, ENE, HOM, and COR of MBF |
| Mean of SS | CON, ENE, HOM, and COR of SS |
| Mean of SI | CON, ENE, HOM, and COR of SI |
| Mean of SAS | CON, ENE, HOM, and COR of SAS |

Figure 2A:
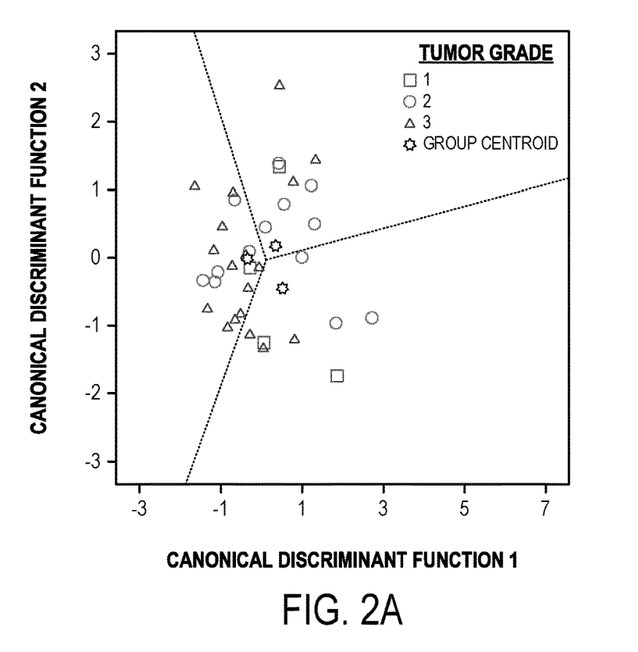
FIG. 2A is an example scatter plot of different tumor grade sampled overlaid on territorial maps over a plane of canonical discriminant functions obtained using the means of four parameters.
Figure 2B:
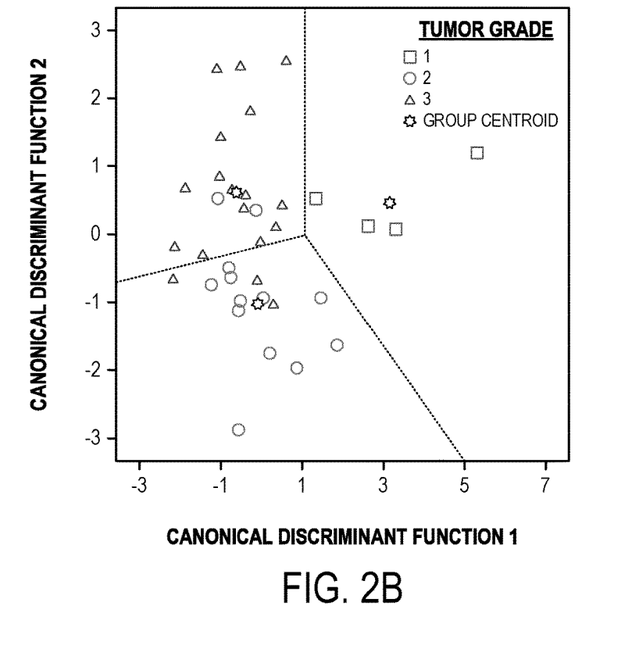
FIG. 2B is an example scatter plot of different tumor grade sampled overlaid on territorial maps over a plane of canonical discriminant functions obtained using second-order statistics of four parameters.
Figure 2C:
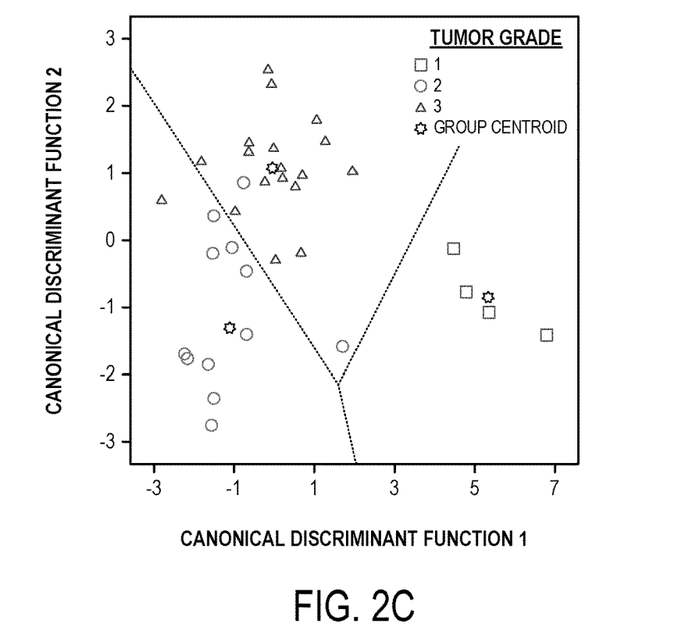
FIG. 2C is an example scatter plot of different tumor grade sampled overlaid on territorial maps over a plane of canonical discriminant functions obtained using both the means and second-order statistics of four parameters.

Examples of two-dimensional scatter plots for quantitative ultrasound data that has been classified using the method described above, and using a discriminant analysis approach, are illustrated in FIGS. 2A-2C. These scatter plots illustrate an example in which the quantitative ultrasound data has been obtained from a population of subjects each having different grades of breast tumors. The axes of the scatter plots define the plane of the canonical discriminant functions acquired. FIG. 2A corresponds to using only the means of MBF, SS, SI, and SAS; FIG. 2B corresponds to using only the CON, ENE, HOM, and COR of MBF, SS, SI, and SAS; and FIG. 2C corresponds to using both the means and CON, ENE, HOM, and COR of MBF, SS, SI, and SAS. Step-by-step enhancements in between-class separability can be observed considering more isolated class centroids, resulting in a reduced number of misclassified samples.

Figure 3:
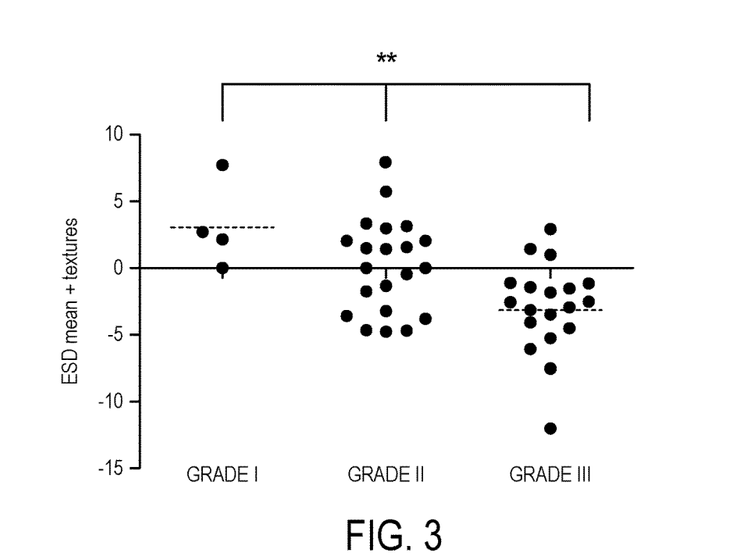
FIG. 3 is an example scatter plot of a linear discriminant analysis function of the mean of effective scatterer diameter ("ESD") combined with contrast, correlation, homogeneity, and energy parameters of the corresponding parametric map.

An example of one-dimensional scatter plot of a linear discriminant function computed using the mean and CON, ENE, HOM, and COR of a single parametric map, the ESD, for a population of subjects with varying grades of breast cancer is illustrated in FIG. 3. This example illustrates that in some instances, the first-order and second-order statistics of a single parametric map can be used to classify tissues or to grade tumors.

Thus, systems and methods for characterizing tissue and grading tumors using first-order and second-order statistical measures of quantitative ultrasound parametric maps have been described. The systems and methods are capable of defining imaging biomarkers based on the first-order and second-order statistical measures of quantitative ultrasound parametric maps and using those imaging biomarkers to classify tissues based on their histological state (e.g., normal, and varying abnormal states). For instance, different pathological breast tissues can be distinguished including normal tissue and Grades I, II, and III invasive carcinoma. Other tissue histological states can also be characterized. For instance, it is contemplated that varying stages of liver fibrosis can be distinguished and characterized using the systems and methods described here.

Dynamic changes in the histological state of tissues can also be characterized by comparing parametric images acquired at different time points. By way of example, the system and methods described here can thus be used to monitor changes in tissue histological state over time. As one example, the changes in tissue histological state can be associated with disease progression, such as a tumor advancing from Grade I to Grade II, or liver fibrosis advancing from a less severe stage to a more severe stage. As another example, the changes in tissue histological state can be associated with a response to a treatment, such as chemotherapy or radiation therapy. In this manner, the systems and methods described here can be used to develop and implement adaptive treatment strategies that are tailored to a particular patient based on their response level to a particular treatment.

The systems and methods described here can also be used to gain a better understanding of the microstructural changes in tissue from one histological state to another. For example, as described by F. L. Lizzi, et al., in "Comparison of theoretical scattering results and ultrasonic data from clinical liver examinations," *Ultrasound in Medicine & Biology*, 1988; 14N:377-385, the SS parameter can be related to ESD, the SI parameter can be related to EAC, and the MBF parameter can be related to both ESD and EAC. As one example, breast tumors generally appear as relatively hypoechoic regions in ultrasound B-mode images, whereas normal tissue typically demonstrates relatively hyperechoic characteristics. However both normal and cancerous breast tissues exhibit heterogeneous patterns in ultrasound B-mode images. In the parametric images described above, lower MBF values can generally be seen in breast tumors compared to normal breast tissue, and the MBF values generally vary with breast tumor grade. The MBF also generally shows contrast between the breast tumor and adjacent tissue. The SS parameter generally varies with breast tumor grade and normal tissue, but is not tumor-specific so there is generally little contrast between breast tumor and adjacent tissue. The SI parameter is generally fairly similar to the SS parameter. The SAS parameter images generally depict a higher SAS value in normal tissue compared to breast tumors. Among breast tumors, there is generally a greater degree of heterogeneity in Grades II and III compared to that of Grade I.

Figure 4:
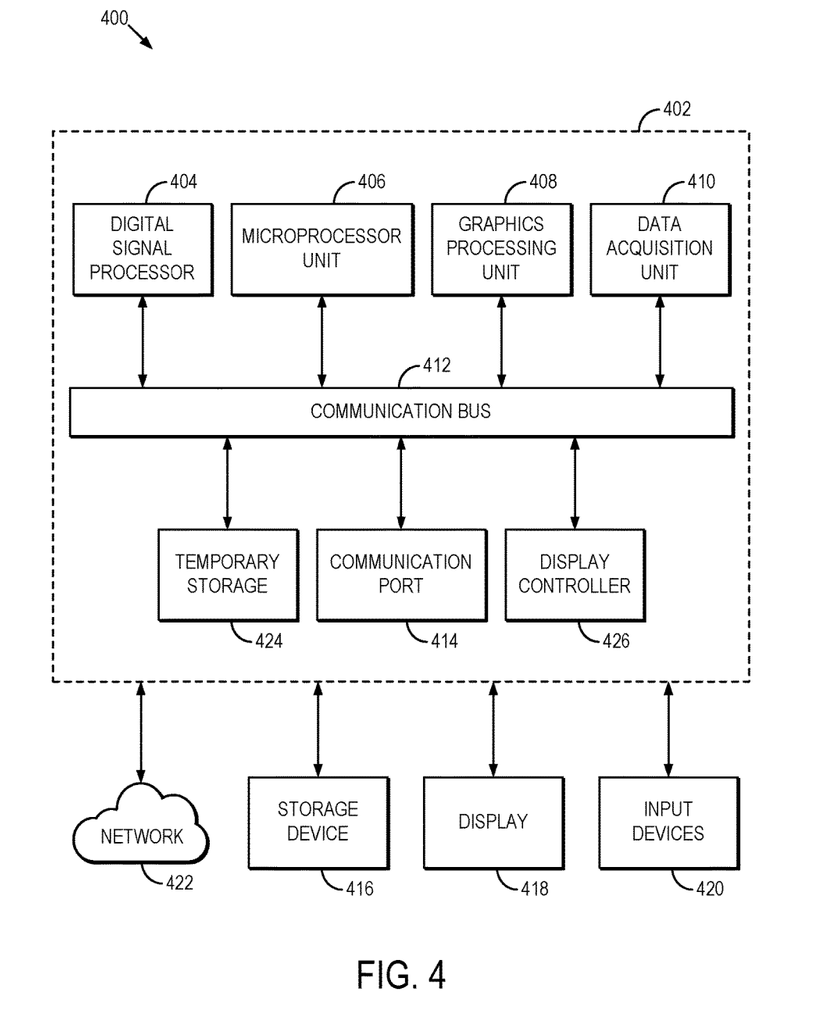
FIG. 4 is a block diagram of an example computer system that can be configured to implement embodiments of the present invention.

Referring now to FIG. 4, a block diagram of an example computer system 400 that can be configured to characterize tissue using the quantitative ultrasound techniques described above, is illustrated. The echo signal data can be provided to the computer system 400 from an ultrasound system, or from a data storage device, and is received in a processing unit 402.

In some embodiments, the processing unit 402 can include one or more processors. As an example, the processing unit 402 may include one or more of a digital signal processor ("DSP") 404, a microprocessor unit ("MPU") 406, and a graphics processing unit ("GPU") 408. The processing unit 402 can also include a data acquisition unit 410 that is configured to electronically receive data to be processed, which may include echo signal data or digital images. The DSP 404, MPU 406, GPU 408, and data acquisition unit 410 are all coupled to a communication bus 412. As an example, the communication bus 412 can be a group of wires, or a hardwire used for switching data between the peripherals or between any component in the processing unit 402.

The DSP 404 can be configured to receive and processes the echo signal data. For instance, the DSP 404 can be configured to receive the echo signal data and form a digital image therefrom. The MPU 406 and GPU 408 can be configured to process the echo signal data, or a digital image formed therefrom, in conjunction with the DSP 404. As an example, the MPU 406 can be configured to control the operation of components in the processing unit 402 and can include instructions to perform processing of the echo signal data, or a digital image formed therefrom, on the DSP 404. Also as an example, the GPU 408 can process image graphics. Also In some embodiments, the DSP 404 can be configured to process the echo signal data, or a digital image formed therefrom, received by the processing unit 402 in accordance with the algorithms described herein. Thus, the DSP 404 can be configured to generate parametric maps, compute first-order and second-order statistical measures of the parametric maps, and characterize tissues based on the first-order and second-order statistical measures.

The processing unit 402 preferably includes a communication port 414 in electronic communication with other devices, which may include a storage device 416, a display 418, and one or more input devices 420. Examples of an input device 420 include, but are not limited to, a keyboard, a mouse, and a touch screen through which a user can provide an input.

The storage device 416 is configured to store echo signal data, digital images, or both, whether provided to or processed by the processing unit 402. The display 418 is used to display images, such as images that may be stored in the storage device 416, and other information. Thus, in some embodiments, the storage device 416 and the display 418 can be used for displaying the parametric maps, and for outputting other information such as data plots or other reports based on statistical measures computed from the parametric maps, including information indicating a characterization of tissues.

The processing unit 402 can also be in electronic communication with a network 422 to transmit and receive data, including echo data, images, and other information. The communication port 414 can also be coupled to the processing unit 402 through a switched central resource, for example the communication bus 412.

The processing unit 402 can also include a temporary storage 424 and a display controller 426. As an example, the temporary storage 424 can store temporary information. For instance, the temporary storage 424 can be a random access memory.

EXAMPLE

Characterizing Fatty Liver

In this example, liver tissue was characterized using the quantitative ultrasound ("QUS") analysis methods described above. The results indicate that the methods are capable of characterizing fatty liver tissue relative to normal liver tissue, thereby providing diagnostic value for evaluating histological states of liver tissues, including whether a particular liver tissue is afflicted by NAFLD.

Materials and methods

Liver Samples. In this example, fresh liver samples were extracted from New Zealand White rabbits. A group of the rabbits consumed a standard chow diet and was used as a control for the study. Another group of the rabbits had been on a special fatty diet, which contained 2% cholesterol and 6% peanut oil, for two weeks, followed by 12 weeks of normal diet. Water was given ad libitum and food was given daily to the rabbits. The feed intake was measured daily and rabbit weights were done weekly. The animals were housed individually in standard stainless steel cages at normal room temperature and light cycles.

Ultrasound Data Acquisition and Processing. Ultrasound images and radio-frequency ("RF") data were collected from the liver specimens, which were completely submerged in phosphate buffered saline ("PBS") solution, within five minutes of the removal of the liver from the body. The specimens were scanned using a Sonix RP system (Ultrasonix, Vancouver, Canada) and a L14-5/38 transducer, with a centre frequency of about 6.5 MHz, and a sampling frequency of 40 MHz. The system was used to collect three-dimensional data with scan plane separations of 0.5 mm.

Ultrasound data were analyzed across scan planes, within a standardized region of interest ("ROI") positioned at the transducer focal depth. Ultrasound RF data analysis was performed using the normalized power spectrum, and textural analysis on QUS parametric maps, to extract quantitative ultrasound spectral and textural parameters (i.e., first-order and second-order statistics of quantitative ultrasound parametric maps).

Power spectra were calculated using a Fourier transform of the raw RF data for each scan line through the ROI and subsequently averaged. The power spectra were corrected for attenuation, with a fixed attenuation coefficient of 0.7 dB/MHz/cm, using a point attenuation compensation approach. In order to remove effects of system transfer functions, the US RF data were normalized using reference data obtained from a tissue-mimicking phantom, through a sliding-window analysis approach. In particular, data were normalized against averaged power spectrum obtained from a glass-bead-embedded agar-gel phantom model, scanned with the same setting used for the liver scans, in order to more accurately account for beam diffraction effects and other instrument-dependent factors, considering the use of a linear array transducer.

Linear regression analysis was performed on the averaged power spectrum within a center frequency-based −6 dB window (bandwidth of 4-9 MHz) to generate a best-fit line. Parameters extracted included the mid-band fit ("MBF"), the spectral slope ("SS"), and the corresponding spectral 0-MHz intercept ("SI"). The parametric maps were generated using the sliding window analysis on a pixel-by-pixel basis, with the parameters calculated for each window and assigned to its centre. The sliding window had a size of 2 mm-by-2 mm.

Texture analysis on QUS parametric maps (e.g., MBF, SS, and SI) was performed on the basis of a gray-level co-occurrence matrix ("GLCM"). Sixteen symmetric GLCMs were constructed considering each pixel's neighbors located at a distance of one to ten pixels with angular values of 0-135 degrees at 45 degree increments. Textural parameters (e.g., homogeneity, contrast, correlation, and energy) were extracted from the corresponding GLCMs of each QUS parametric map and were subsequently averaged.

Statistical Analysis and Tissue Categorization. Statistical analyses were applied in order to evaluate if normal and fatty livers demonstrate statistically significant differences in first and second order statistics of QUS parametric maps. Statistical test of significance were conducted using a t-test (unpaired, two-sided, 95 percent confidence). Linear discriminant analyses ("LDA") were performed using different combinations of QUS spectral parameters (first-order statistics of QUS parametric maps) and textural parameters (second-order statistics of QUS parametric maps) in order to differentiate between normal and fatty liver samples non-invasively. A step-wise linear discriminant analysis was performed, using the most significant QUS spectral and textural parameters, in order to determine an optimized combination of QUS parameters for categorizing liver tissue more robustly.

Results

Quantitative ultrasound parametric maps could provide favorable contrasts between normal and fatty liver tissues, as observed in this study.

Figure 5:
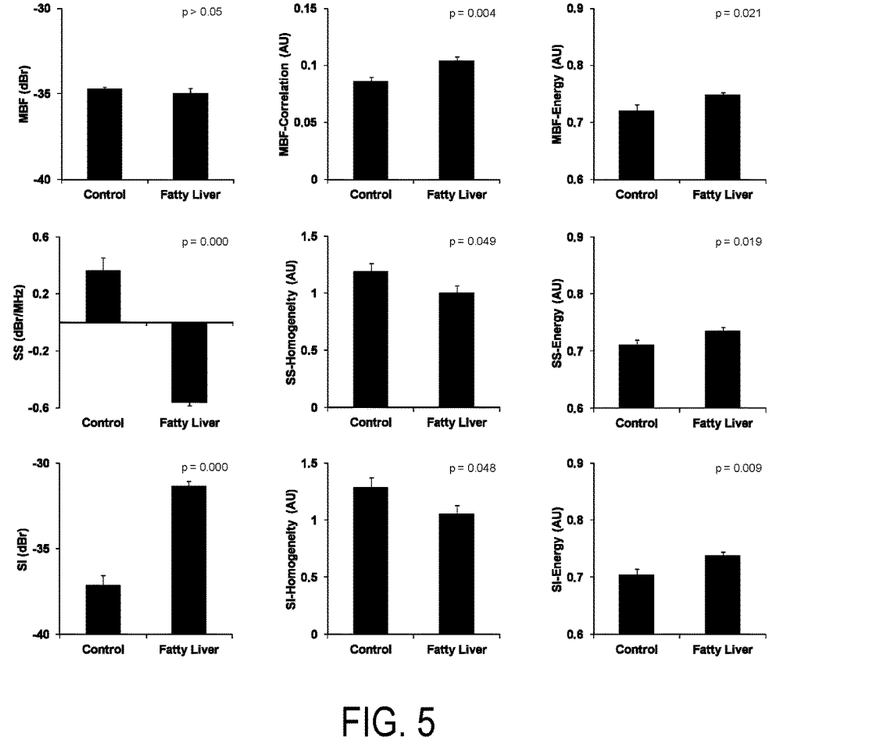
FIG. 5 illustrates a series of plots of average values of different QUS spectral (first-order) and textural (second-order) parameters obtained for normal (control) and fatty livers.

FIG. 5 demonstrates average values of single QUS spectral and textural parameters, obtained for normal and fatty livers, respectively. MBF-Correlation and MBF-Energy demonstrated statistically significant differences between the two tissue types, whereas no significant differences were observed in the mean values of the MBF parameter. Also SS, SS-Homogeneity, SS-Energy, SI, SI-Homogeneity, and SI-Energy showed statistically significant differences between the normal and fatty liver specimens.

Figure 6A:
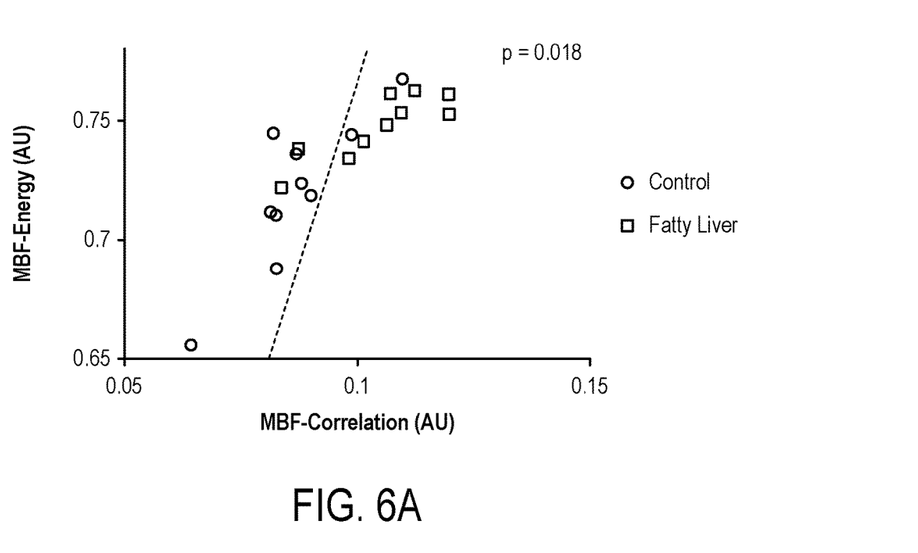
FIG. 6A is an example scatter plot on a plane of MBF energy and MBF correlation parameters with data obtained for normal (control) and fatty livers, where samples for the two tissue types were classified using linear discriminant analysis on the combined parameters associated with the plane and the classification border is illustrated as the dashed line.
Figure 6B:
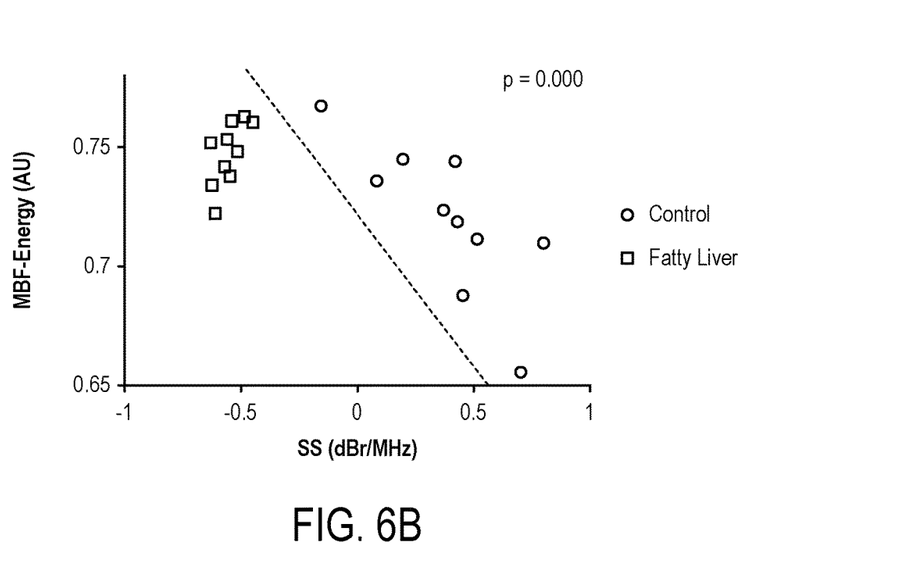
FIG. 6B is an example scatter plot on a plane of MBF energy and SS parameters with data obtained for normal (control) and fatty livers, where samples for the two tissue types were classified using linear discriminant analysis on the combined parameters associated with the plane and the classification border is illustrated as the dashed line.
Figure 6C:
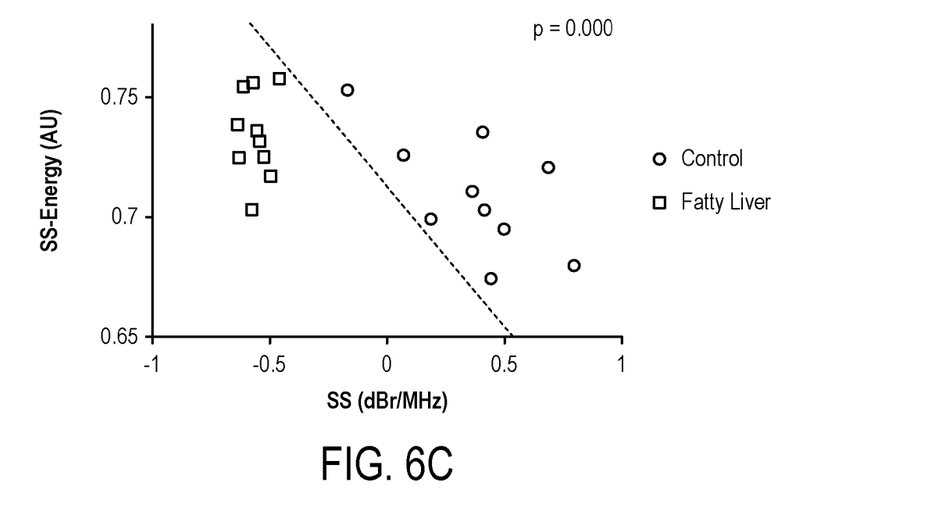
FIG. 6C is an example scatter plot on a plane of SS energy and SS parameters with data obtained for normal (control) and fatty livers, where samples for the two tissue types were classified using linear discriminant analysis on the combined parameters associated with the plane and the classification border is illustrated as the dashed line.
Figure 6D:
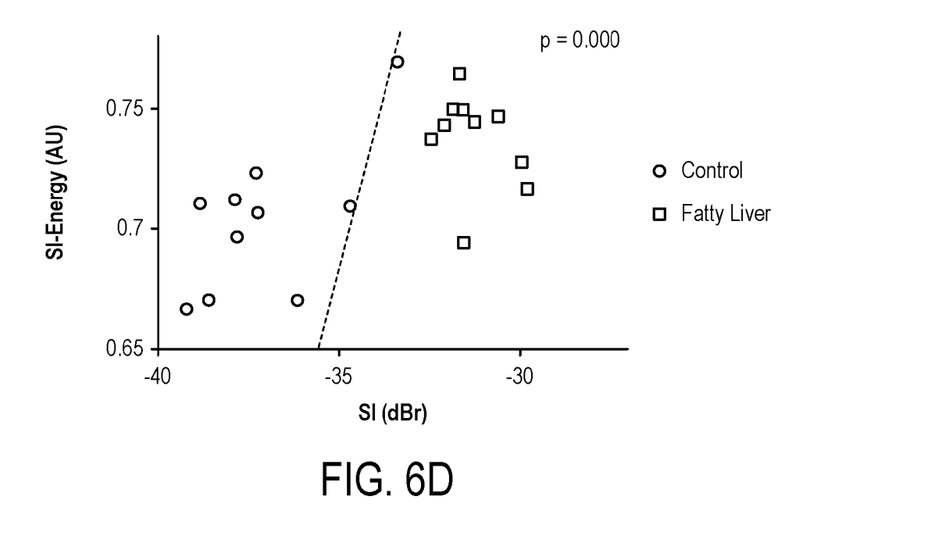
FIG. 6D is an example scatter plot on a plane of SI energy and SI parameters with data obtained for normal (control) and fatty livers, where samples for the two tissue types were classified using linear discriminant analysis on the combined parameters associated with the plane and the classification border is illustrated as the dashed line.

FIGS. 6A-5D are scatter plots of data on different planes of QUS spectral and textural parameters. Samples of the two liver-tissue types have been classified using linear discriminant analyses on the combined parameters associated with each plane. The classification borders have been presented with dash lines. A sensitivity and specificity of 80 percent was obtained for detecting fatty liver samples using MBF-Correlation and MBF-Energy in a combination (p=0.018). SS and SS-Energy combined parameters resulted in a sensitivity and specificity of 100 percent (p=0.000), whereas SI and SI-Energy parameters, in a combination, resulted in a sensitivity of 100 percent and a specificity of 95 percent (p=0.000). A step-wise linear discriminant analysis was performed using all the six QUS parameters mentioned above, in order to obtain an optimized classification plane providing a more robust separability between the two tissue-type samples. The step-wise analysis resulted in a combination of the MBF-Energy and the SS, as a hybrid QUS parameter, with a sensitivity and specificity of 100 percent (p=0.000) for detecting fatty liver specimens.

The present invention has been described in terms of one or more preferred embodiments, and it should be appreciated that many equivalents, alternatives, variations, and modifications, aside from those expressly stated, are possible and within the scope of the invention.

The invention claimed is:
1. A method for classifying a tissue as being associated with a particular histological state using an ultrasound system, the steps of the method comprising:
 a) acquiring ultrasound echo signal data from a region-of-interest that contains the tissue using the ultrasound system;
 b) producing at least one parametric map from the acquired ultrasound echo signal data, the at least one parametric map having pixel values associated with a parameter computed from the acquired ultrasound echo signal data;
 c) computing at least one first-order statistical measure of the at least one parametric map;
 d) computing at least one second-order statistical measure of the at least one parametric map; and
 e) classifying the tissue as being associated with a particular histological state using the computed at least one first-order statistical measure and the computed at least one second-order statistical measure.

2. The method as recited in claim 1 in which the at least one parametric map has pixel values associated with a parameter that includes at least one of mid-band fit, spectral slope, spectral 0-MHz intercept, spacing among scatterers, effective scatterer diameter, and effective acoustic concentration.

3. The method as recited in claim 1 in which the at least one first-order statistical measure computed in step c) is at least one of mean, standard deviation, skewness, and kurtosis.

4. The method as recited in claim 1 in which the at least one second-order statistical measure computed in step d) is at least one of contrast, energy, homogeneity, correlation, autocorrelation, dissimilarity, gray-level co-occurrence matrix variability, entropy, cluster shade, cluster prominence, and maximum probability.

5. The method as recited in claim 1 in which the histological state is at least one of a normal histological state and an abnormal histological state.

6. The method as recited in claim 5 in which the abnormal histological state indicates the tissue as cancerous.

7. The method as recited in claim 6 in which step e) further includes determining a tumor grade of the tissue using the computed at least one first-order statistical measure and the computed at least one second-order statistical measure when the tissue is classified as being associated with the abnormal histological state that indicates the tissue as cancerous.

8. The method as recited in claim 5 in which the tissue is liver tissue and the abnormal histological state indicates at least one of liver fibrosis, non-alcoholic fatty liver disease (NAFLD), cirrhosis, and ischemic liver damage.

9. The method as recited in claim 8 in which step e) further includes determining a liver fibrosis stage of the liver tissue using the computed at least one first-order statistical measure and the computed at least one second-order statistical measure when the liver tissue is classified as being associated with the abnormal histological state that indicates liver fibrosis.

10. The method as recited in claim 1 in which step e) includes performing a discriminant analysis on the computed at least one first-order statistical measure and the computed at least one second-order statistical measure.

11. The method as recited in claim 10 in which the discriminant analysis is a linear discriminant analysis.

12. The method as recited in claim 1 in which step b) includes computing a normalized power spectrum of the ultrasound echo signal data and producing the at least one parametric map by computing the parameter from the normalized power spectrum.

13. The method as recited in claim 12 in which step b) includes providing reference echo signal data obtained from a phantom using the ultrasound system and computing the normalized power spectrum using the provided reference echo signal data such that effects from the ultrasound system are minimized in the normalized power spectrum.

14. The method as recited in claim 1 further comprising the step of determining a change in histological state of the tissue by comparing the particular histological state of the tissue with a previously known histological state of the tissue.

15. The method as recited in claim 14 further comprising the step of determining a treatment strategy when the determined change in histological state indicates a particular response of the tissue to a previous treatment.

16. The method as recited in claim 15 in which the determined change in histological state indicates apoptosis.

17. The method as recited in claim 14 in which the determined change in histological state indicates a transition between disease stages.

18. The method as recited in claim 17 in which the transition between disease stages indicated a transition between at least one of tumor grades and liver fibrosis stages.

19. A method for generating an imaging biomarker that is indicative of a histological state of a tissue using an ultrasound system, the steps of the method comprising:
 a) acquiring ultrasound echo signal data from a tissue using the ultrasound system;
 b) producing at least one parametric map from the acquired ultrasound echo signal data, the at least one parametric map having pixel values associated with a parameter computed from the acquired ultrasound echo signal data;
 c) computing at least one first-order statistical measure of the at least one parametric map;
 d) computing a plurality of second-order statistical measures of the at least one parametric map; and
 e) generating an imaging biomarker by determining a combination of the computed at least one first-order statistical measure and the computed plurality of second-order statistical measures that is correlated with a desired accuracy of classifying the tissue as being associated with a particular histological state.

* * * * *